United States Patent
Tal

(10) Patent No.: US 6,962,575 B2
(45) Date of Patent: Nov. 8, 2005

(54) SINGLE ACCESS DIALYSIS NEEDLE

(75) Inventor: Michael Tal, Woodbridge, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/358,634

(22) Filed: Feb. 5, 2003

(65) Prior Publication Data

US 2003/0158514 A1 Aug. 21, 2003

Related U.S. Application Data

(60) Provisional application No. 60/354,467, filed on Feb. 5, 2002.

(51) Int. Cl.[7] .............................................. A61M 29/00
(52) U.S. Cl. .................. 604/107; 604/6.05; 604/164.01
(58) Field of Search ................................ 604/104–109, 604/164.01, 164.03, 164.08, 164.1, 164.11, 164.12, 165.01, 165.02, 158, 162–163, 6.05, 6.06, 6.16, 4.01, 5.01, 8; 210/646, 257.1–257.2

(56) References Cited

U.S. PATENT DOCUMENTS

| | | | | |
|---|---|---|---|---|
| 3,833,003 A | | 9/1974 | Taricco | |
| 3,946,741 A | * | 3/1976 | Adair | 604/105 |
| 4,037,599 A | * | 7/1977 | Raulerson | 604/44 |
| RE29,346 E | | 8/1977 | Kopp | |
| 4,096,860 A | * | 6/1978 | McLaughlin | 604/44 |
| 4,098,275 A | | 7/1978 | Consalvo | |
| 4,134,402 A | | 1/1979 | Mahurkar | |
| 4,299,217 A | * | 11/1981 | Sagae et al. | 604/44 |
| 4,468,216 A | * | 8/1984 | Muto | 604/43 |
| 4,540,402 A | * | 9/1985 | Aigner | 604/44 |
| 4,585,446 A | | 4/1986 | Kempf | |
| 4,808,163 A | * | 2/1989 | Laub | 604/105 |
| 4,940,455 A | | 7/1990 | Guinn | |
| 5,053,004 A | * | 10/1991 | Markel et al. | 604/43 |
| 5,122,122 A | * | 6/1992 | Allgood | 604/174 |
| 5,197,971 A | * | 3/1993 | Bonutti | 606/192 |
| 5,219,335 A | | 6/1993 | Willard et al. | |
| 5,301,682 A | * | 4/1994 | Debbas | 600/550 |
| 5,421,825 A | | 6/1995 | Farcot | |
| 5,662,619 A | | 9/1997 | Zarate | |
| 5,702,365 A | * | 12/1997 | King | 604/105 |
| 5,707,362 A | * | 1/1998 | Yoon | 604/164.03 |
| 5,807,329 A | | 9/1998 | Gelman | |
| 5,857,999 A | * | 1/1999 | Quick et al. | 604/107 |
| 5,882,340 A | * | 3/1999 | Yoon | 604/164.12 |
| 5,976,103 A | * | 11/1999 | Martin | 604/43 |

\* cited by examiner

Primary Examiner—LoAn H. Thanh
(74) Attorney, Agent, or Firm—Welsh & Flaxman LLC

(57) ABSTRACT

A single access dialysis needle system comprises a first cannula, a second cannula or sheath, and a barrier arranged on the outer surface of the first cannula. The distal end of the first cannula extends distal to the distal end of the second cannula or outer sheath, and the barrier is positioned between the respective distal ends. When the barrier is inflated or otherwise activated, it prevents or minimizes recirculation.

17 Claims, 4 Drawing Sheets

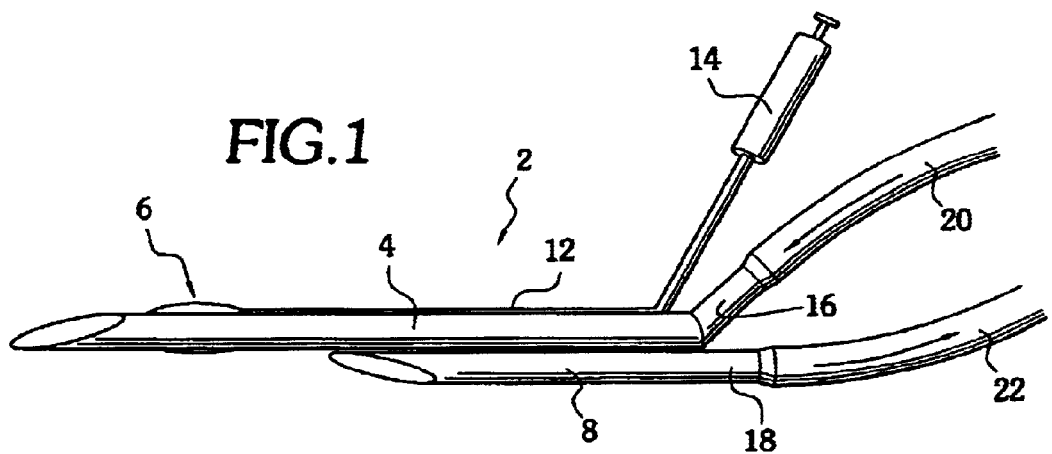
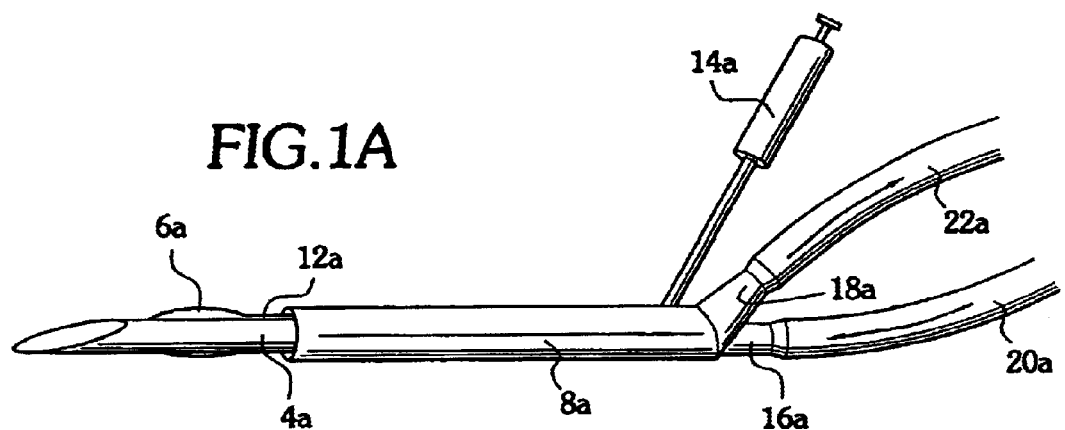
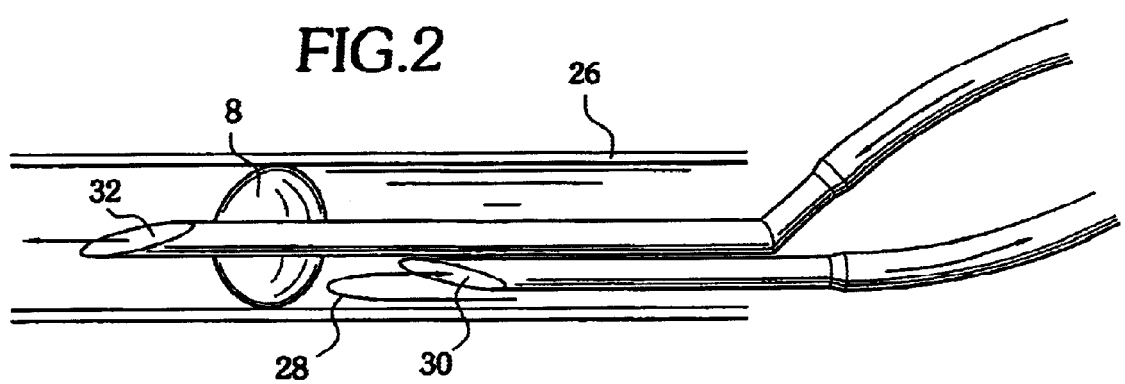

SINGLE ACCESS DIALYSIS NEEDLE

CROSS-REFERENCE TO RELATED APPLICATION

This application is based upon now abandoned U.S. provisional patent application Ser. No. 60/354,467, filed Feb. 5, 2002, incorporated herein by reference.

FIELD OF THE INVENTION

The invention relates to extracorporeal hemodialysis. More particularly, the invention related to a method and apparatus for dialyzing a patient's blood with a single venipuncture or cannulation.

BACKGROUND OF THE INVENTION

Historically, kidney diseases have been of critical concern to human life. Many kinds of kidney diseases interfere with the function of the kidney such that the kidney ceases to remove waste and excess water from the blood. When the kidney is sufficiently impaired that large portions of the waste products and water are not removed from the blood, the life of the patient cannot be preserved unless a way is provided for artificially performing the function of the impaired kidney. Even today, the same general procedure is used for dialyzing patients' blood that was used very early in the treatment of kidney disease.

For example, the most commonly accepted practice for dialyzing a patient's blood extracorporeally requires the surgical creation of a subcutaneous, arterio-venous fistula. Thereafter, the subcutaneous venous system dilates secondary to the increase of blood flow derived from the artery to the vein through the fistula. Sufficient blood flow for dialysis is then obtainable by venipuncture with large bore needles. Normally, two hollow needles or cannulas are used to perform two venipunctures on the patient so that two blood-communication sites exist simultaneously in the patient. Conventionally, blood is withdrawn from one of the punctured blood vessels, forced through a hemodialyzer and thereafter forced into the other. The needles have to be substantially distant from one another to prevent recirculation of blood.

The aforementioned procedure has been found to have serious disadvantages both to the patient and to the attending physicians, nurses, and technicians. The problems are particularly aggravated because most patients requiring extracorporeal hemodialysis must undergo treatment as frequently as three to four times per week. This means that if every venipuncture were completely successful, a patient would need to undergo from 6 to 8 venipunctures or cannulations each week.

It is well-known that the duration and well-function of a fistula created by venipuncture is inversely related to the number of venipunctures. Tissue repeatedly subjected to the trauma of venipuncture is much more susceptible to thrombophlebitis, paravascular hemorrhage, clotting and infection. In fact, it is commonly found in patients who have experienced a number of venipunctures, that the tissues surrounding the most accessible veins develop large hematomas which obscure the veins, making successful venipuncture extremely difficult because of insufficient blood flow in the damaged blood vessels.

Also contributing to the problem is the fact that once one successful venipuncture is made and blood is allowed to flow from the patient's body toward a hemodialyzer, the blood volume in the patient's body is reduced, making the second venipuncture very difficult. It has historically been found that while most skilled physicians or technicians are able to perform the first venipuncture with little difficulty, frequently a plurality of attempts is necessary before a second venipuncture can be performed on the same patient.

In addition, while the pain and discomfort suffered by a hemodialysis patient is understandable, the multiple attempts at venipuncture often necessary to place the second needle result in increasing apprehension, and anxiety on the part of both the patient and the physician, nurse, or technician attending the patient further reduces the likelihood of successful venipuncture.

SUMMARY OF THE INVENTION

The present invention, including a novel method and apparatus, reduces patient trauma and tissue damage by accommodating extracorporeal hemodialysis with a single venipuncture. Generally, once the venipuncture has been performed, blood is conducted away from the venipuncture site through one passageway in a double-lumen needle system. The blood is forced through the extracorporeal hemodialyzer and thereafter through the other passageway of the double-lumen needle system again to the venipuncture site. The current invention also reduces recirculation by preventing blood returned to a graft from being aspirated back into the hemodialyzer. A mechanical barrier, membrane, or other structure, such as a balloon, physically substantially separates blood that enters one needle from the blood exiting the other needle.

In another embodiment of the invention, an access needle system comprises a cannula, a sheath around the cannula to form an annular space, and a hemostasis valve surrounding at least the proximal end of the cannula and being in fluid communication with the annular space. The sheath has one or more lateral ports or openings, and hoses in fluid communication with the proximal end of the cannula and the hemostasis valve or the annular space extend to a blood hemodialyzer. Preferably there will be a barrier to block or partially obstruct fluid flow. The barrier may comprise an inflatable balloon membrane, or other mechanical structure. Optionally a second sheath may partly surround the first sheath and uncover the one or more ports in the inner sheath when the outer sheath is moved proximally. Alternatively, the outer sheath may have one or more lateral pores that may align with one or more lateral pores of the first sheath when the second sheath is slid along the first sheath. Accordingly, both the proximal end of the first sheath and outer sheath and the annular space may be in fluid communication with the same opening.

OBJECTS OF THE INVENTION

It is a primary object of the present invention to provide an improved method of extracorporeal hemodialysis using a single venipuncture for each treatment.

It is another object of the present invention to provide an improved apparatus facilitating extracorporeal hemodialysis with a single venipuncture.

It is yet a further object of the present invention to provide a single access dialysis needle having two lumens and a barrier wherein extracorporeal homodialysis can be performed using a single venipuncture.

These and other objects and features of the present invention will become more fully apparent from the description below.

BRIEF DESCRIPTION OF THE DRAWINGS

FIG. 1 is a partly cross-sectional schematic view of an embodiment of the system of the invention for dialyzing a patient's blood using a single venipuncture;

FIG. 1A is a partly cross-sectional schematic view of a variation of the embodiment shown in FIG. 1 where the two cannulae are coaxial;

FIG. 2 is a schematic illustration of a portion of the system shown in FIG. 1 in position in a patient's dialysis conduit;

DETAILED DESCRIPTION OF INVENTION

Figure 3:
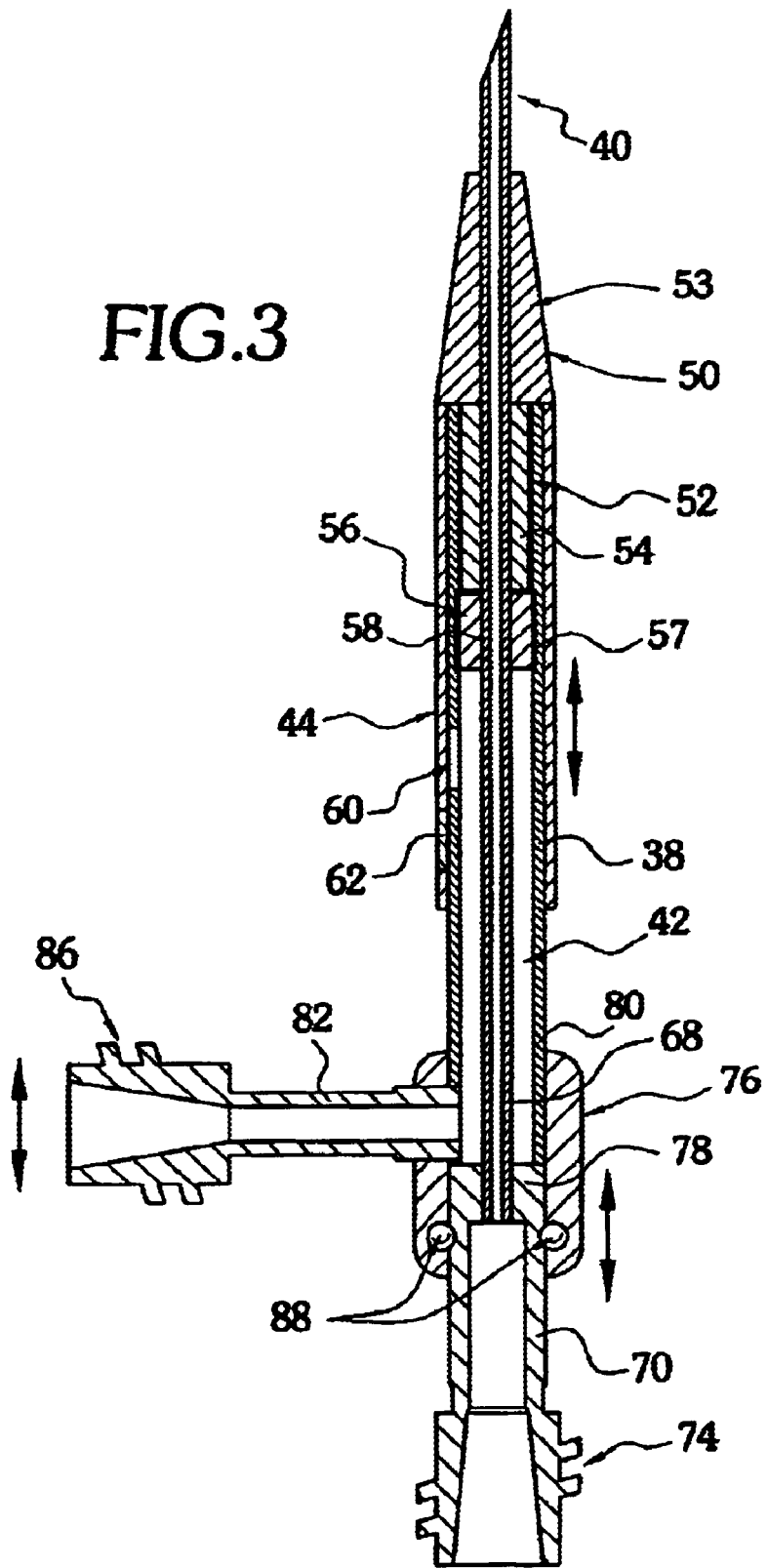
FIG. 3 is a cross-sectional view of another embodiment of the system of the invention where at least one sheath is arranged circumferentially around a cannula.

The invention can perhaps be better understood from the drawings. In FIG. 1 a dialysis needle system 2 comprises a first cannula 4 with an annular balloon 6 and a second cannula 8. Balloon 6 is in fluid communication with an inflation lumen 12 and an inflator 14. Balloon 6 is deployed after insertion of the cannula and positioning within a dialysis fistula. The proximal end 16 of first cannula 4 and the proximal end 18 of second cannula 8 are separated or otherwise configured so that each of proximal ends 16 and 18 can be attached to hoses 20, 22 attached to a hemodialyzer (not shown). First cannula 4 and second cannula 8 are shown in FIG. 1 to be essentially parallel. It should be noted that it is within the scope of the invention that first cannula 4 and second cannula 8 can be coaxial to one another. For example, as shown in FIG. 1A, second cannula 8a circumferentially surrounds first cannula 4a. Balloon 6a is in fluid communication with an inflation lumen 12a and an inflator 14a. Balloon 6a is deployed after insertion of the needle system and positioning within a dialysis fistula. The proximal end 16a of first cannula 4a and the proximal end 18a of second cannula 8a are separated or otherwise configured so that each of proximal ends 16a and 18a can be attached to hoses 20a, 22a attached to a hemodialyzer (not shown).

Needle system 2 is shown in FIG. 2 in position in a patient's dialysis conduit or vessel 26. Annular balloon 6 is inflated to cause blood flow in dialysis conduit 26 to go in the direction of arrows 28 into a lumen 30 of second cannula 8. Blood flows into hose 22, to a hemodialyzer (not shown), through hose 20, and then into a lumen 32 of first cannula 4. Annular balloon 8 functions to stop the flow of blood and separate the blood streams into and out of dialysis needle system 2, thereby preventing recirculation of blood. It is within the scope of the invention that blood could also flow in the opposite direction, that is, in the directions opposite to the arrows shown in FIG. 2.

In the embodiment of the invention shown in FIG. 3, a first or inner sheath 38 is circumferentially arranged around a cannula or needle 40 to form annular space 42, and optionally a second or outer sheath 44 is circumferentially and slidably arranged around inner sheath 38. The distal portion 52 of inner sheath 38 is sealingly attached to dilating member 50, which surrounds the distal portion 53 of cannula 40.

Adjacent to dilating member 50 is an annular support member 54 through which cannula 40 extends. Support member 54 is affixed to or integral with dilating member 50 and provides support for sheath distal portion 52.

Figure 5:
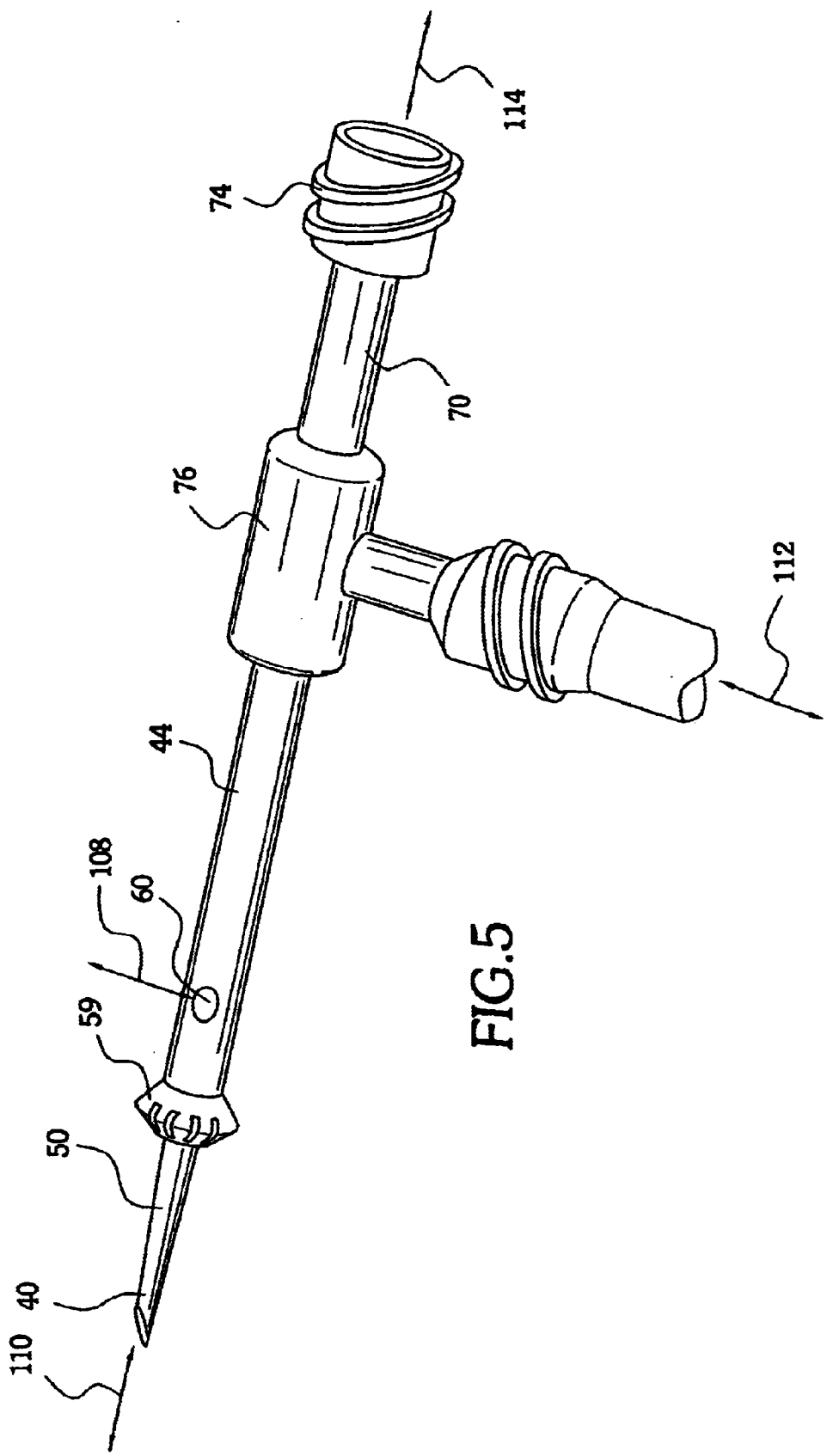

Inner sheath 38 preferably has an expandable section 56 having longitudinal cut or score lines 57, for example, from at least about 4 to about 20, or more, such cut or score lines and optionally a latitudinal score line 58. When sheath 38 is pushed or slid distally, section 56 forms a barrier structure 59 in the radial direction, as shown in FIG. 5. If outer sheath 44 is used, it is slid proximally to expose barrier section 56 and at least one opening 60. Alternatively, an opening 60 in inner sheath 38 could become aligned with an opening 62 in outer sheath 44 when sheath 44 is moved in the proximal direction. For example, the inner sheath 38 and outer sheath 44 and the annular space 42 is in fluid communication with the opening 62.

Figure 4:
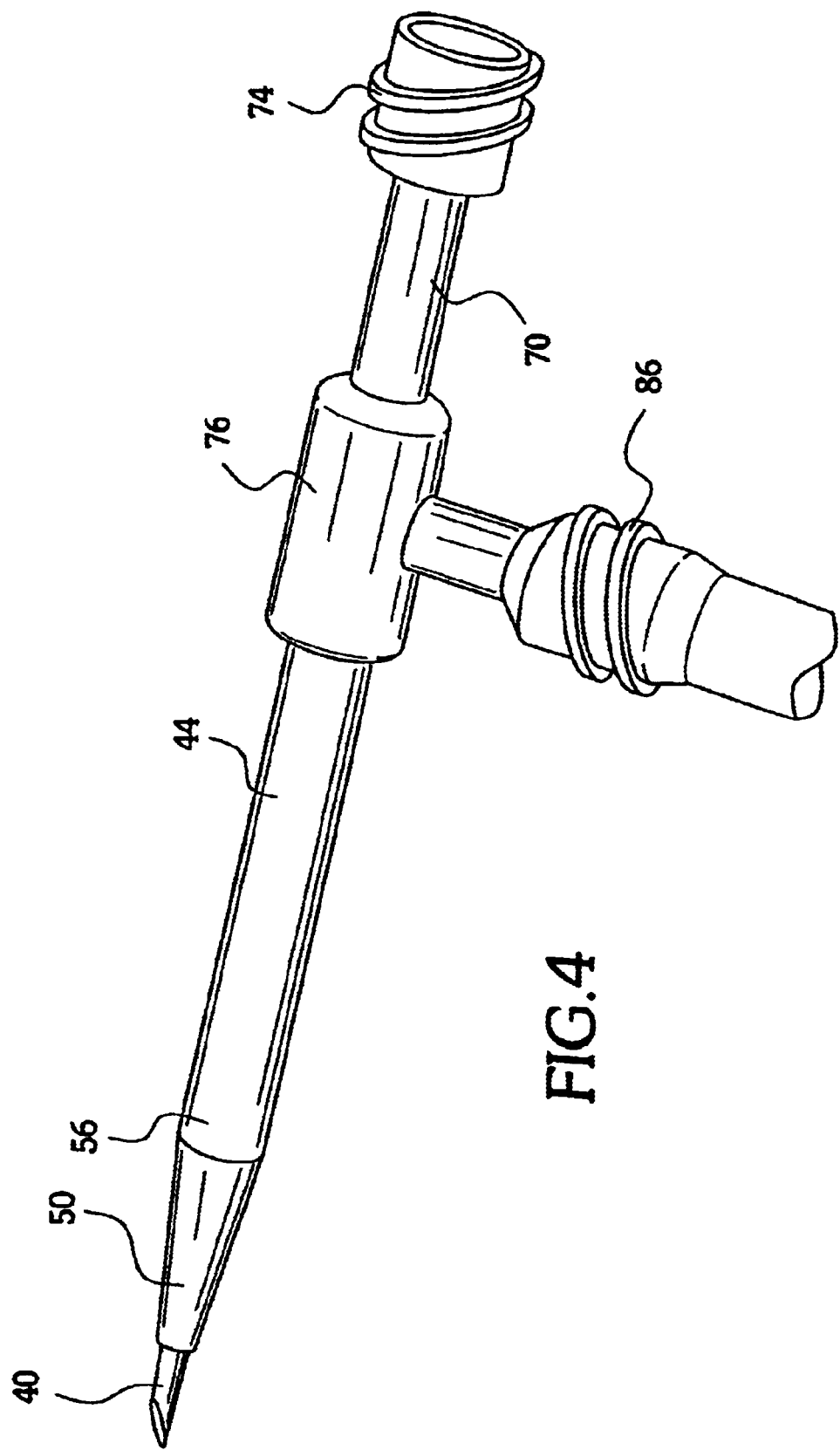
FIGS. 4 and 5 are each an oblique view of the embodiment shown in FIG. 3.

It is within the scope of the invention that the embodiment of the invention shown in FIGS. 3 to 5 may have a barrier element other than the structure described above. For example, this embodiment may have an inflatable balloon with an inflation lumen and an inflator, as described for needle system 2. Other barrier structure known now or to be developed would be similarly operable.

The proximal end 68 of cannula 40 is in fluid communication with a stationery shaft 70, which is connected to a flexible hose (not shown) which preferably has a threaded luer connector 74 at its proximal end. A hemostasis valve 76 slidably encompasses the distal end 78 of stationary shaft 70 and the proximal portion 80 of inner sheath 38. Also, hemostasis valve 76 is in fluid communication with a port 82, which is connected to a flexible hose (not shown) which preferably has a luer connector 86 at its proximal end. Preferably hemostasis valve 76 has at least one sealing ring 88, such as an O-ring or a rubber membrane, on or in the surface adjacent shaft 70. Preferably valve 76 is affixed to the proximal portion 80 of inner sheath 38. Both luer connectors 74, 86 are intended to connect to a hemodialysis machine (not shown).

FIGS. 4 and 5 are each an oblique view of the embodiment of the invention depicted in FIG. 3. In FIG. 4 outer sheath 44 is in its initial position relative to inner sheath 38, where port 60 in inner sheath 38 and barrier structure section 56 are covered.

If outer sheath 44 is used, it is moved longitudinally in the proximal direction, for example, by gripping the outer surface of outer sheath 44, and then port 60 in sheath 38 and expandable section 56 are uncovered. Hemostasis valve 76 and the proximal portion 80 of inner sheath 38 are displaced in the distal direction to cause distal section 56 to expand radially to form barrier structure 59. Blood flow is represented by arrows 108, 110, 112, and 114.

The device of the invention comprises conventional physiologically acceptable materials, especially those that can be sterilized, as would be appreciated by those skilled in the art. Typically the components described herein will be made from rigid or slightly flexible polymers and/or co-polymers, several as polypropylene, polyethylene, polystyrene, polybutylene, and co-polymers thereof. Sealing ring 88 would preferably be comprised of a suitable flexible polymer, rubber or elastomer.

The outer surface of the device should be configured or designed to minimize friction or interference with movement or body surfaces or tissue. The outer surfaces of the device according to the invention should be as smooth as possible. For example, the distal surface 92 of hemostasus valve 76 can be rounded as in FIG. 3 or tapered as shown in FIGS. 4 and 5.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

I claim:

1. A single access dialysis needle system comprising:
   a cannula having a proximal end and a distal end, and a lumen extending longitudinally between the proximal end and the distal end, the lumen including a distal opening at the distal end and a proximal opening at the proximal end such that fluid may exit and enter the cannula,
   a sheath arranged circumferentially around the cannula to form an annular lumen between the cannula and the sheath, the sheath having a proximal end and a distal end, the sheath further includes a lateral port located substantially between the proximal end and distal end of the sheath and in fluid communication with the annular lumen which provides for the flow of fluid between an outer surface of the sheath and the annular lumen, and
   a barrier capable of being deployed to extend substantially radially from the sheath to block or substantially obstruct fluid flow, radial expansion of the barrier being controlled by movement of the sheath, wherein the distal opening of the cannula is distal to the barrier and the port of the sheath is proximal to the barrier,
   wherein the lumen at the proximal end of the cannula and the annular lumen are adapted for connection to a blood hemodialyzer.

2. The needle system of claim 1, wherein the barrier is a structural or mechanical barrier.

3. The needle system of claim 2, wherein the barrier is in functional communication with an actuator to cause the barrier to activate.

4. A single access dialysis needle system comprising:
   a cannula having a proximal end and a distal ends, and a lumen extending between the proximal end and the distal end, the lumen including a distal opening at the distal end and a proximal opening at the proximal end such that fluid may exit and enter the cannula,
   an inner sheath arranged circumferentially around the cannula to form an annular lumen between the cannula and the inner sheath, the inner sheath having a proximal end and a distal end, the inner sheath further includes a port in fluid communication with the annular lumen which provides for the flow of fluid between an outer surface of the inner sheath and the annular lumen,
   an outer sheath arranged circumferentially around the inner sheath and having a proximal end and a distal end, and
   barrier capable of being deployed to extend substantially radially from the outer sheath to block or substantially obstruct fluid flow, wherein the distal opening of the cannula is distal to the barrier and the port of the inner sheath is proximal to the barrier,
   wherein the lumen at the proximal end of the cannula and the annular lumen are adapted for connection to a blood hemodialyzer.

5. The needle system of claim 4, wherein the outer sheath can be moved slidably over the inner sheath.

6. The needle system of claim 4, wherein the outer sheath slides over the inner sheath in only the longitudinal direction.

7. A single access dialysis needle system comprising:
   a cannula having a proximal end and a distal end, and a lumen extending therethrough,
   an inner sheath arranged circumferentially around the cannula to form an annular lumen between the cannula and the inner sheath, the inner sheath having a proximal end and a distal end,
   an outer sheath arranged circumferentially around the inner sheath and having a proximal end and a distal end, and
   a barrier capable of being deployed to extend substantially radially from the outer sheath to block or substantially obstruct fluid flow,
   wherein the proximal end of the cannula and the annular lumen are adapted for connection to a blood hemodialyzer, and the inner sheath and the outer sheath each have one or more lateral openings.

8. The needle system of claim 7, wherein the lateral openings are positioned so that the outer sheath can be slid over the inner sheath to cause at least two lateral openings to align.

9. The needle system of claim 4, wherein the barrier blocks or partially obstructs blood in a blood vessel.

10. The needle system of claim 4, wherein the barrier is a structural or mechanical barrier.

11. The needle system of claim 10, wherein the barrier is in functional communication with an actuator to cause the barrier to activate.

12. A single access dialysis needle system comprising:
    a cannula having a proximal end and a distal end, and a lumen extending therethrough,
    an inner sheath arranged circumferentially around the cannula to form an annular lumen between the cannula and the inner sheath, the inner sheath having a proximal end and a distal end,
    an outer sheath arranged circumferentially around the inner sheath and having a proximal end and a distal end, and
    a barrier capable of being deployed to extend substantially radially from the outer sheath to block or substantially obstruct fluid flow,
    wherein the proximal end of the cannula and the annular lumen are adapted for connection to a blood hemodialyzer, and, wherein the distal end of the cannula comprises a dilating member arranged circumferentially around said distal end.

13. The needle system of claim 12, wherein the distal end of the inner sheath is affixed to or integral with the dilating member.

14. The needle system of claim 13, wherein the distal end of the outer sheath is affixed to or integral with the dilating member.

15. The needle system of claim 13, wherein hemostasis valve is circumferentially arranged around the proximal end of the cannula, the proximal end of the inner sheath, or both.

16. The needle system of claim 15, wherein the hemostasis valve is in fluid communication with a port.

17. The needle system of claim 15, wherein the hemostasis valve can be moved in a longitudinal direction relative to the needle, the inner sheath, or both.

* * * * *